| United States Patent [19] | [11] Patent Number: 4,812,591 |
| Buysch et al. | [45] Date of Patent: Mar. 14, 1989 |

[54] PROCESS FOR THE PREPARATION OF BISPHENOL-BISACRYLATES

[75] Inventors: Hans-Josef Buysch; Werner Klöker, both of Krefeld, Fed. Rep. of Germany

[73] Assignee: Bayer Aktiengesellschaft, Leverkusen, Fed. Rep. of Germany

[21] Appl. No.: 232,232

[22] Filed: Aug. 15, 1988

[30] Foreign Application Priority Data

Aug. 25, 1987 [DE] Fed. Rep. of Germany ....... 3728302

[51] Int. Cl.$^4$ .............................................. C07C 09/00
[52] U.S. Cl. .................................................... 560/140
[58] Field of Search ........................................ 560/140

[56] References Cited

U.S. PATENT DOCUMENTS

| 4,143,064 | 3/1979 | Loeffler et al. ............ 560/140 |
| 4,182,725 | 1/1980 | Floyd et al. ............... 560/140 |
| 4,199,517 | 3/1980 | Monte et al. .............. 560/140 |
| 4,239,803 | 12/1980 | Ohzeki et al. ............ 560/140 |
| 4,683,241 | 9/1987 | Miyano et al. ............ 560/140 |

FOREIGN PATENT DOCUMENTS

| 63541 | 3/1987 | Japan . |
| 738954 | 10/1955 | United Kingdom ........ 560/140 |

OTHER PUBLICATIONS

Kawaguchi, Milul Shika Zairyo, Kikai 2(3) 298–301, 1983.

*Primary Examiner*—Paul J. Killos
*Attorney, Agent, or Firm*—Connolly and Hutz

[57] ABSTRACT

This invention relates to a process for the preparation of bisphenol-bisacrylates by the reaction of bisphenols with acrylic acid halides in the presence of bases.

6 Claims, No Drawings

PROCESS FOR THE PREPARATION OF BISPHENOL-BISACRYLATES

This invention relates to a process for the preparation of bisphenol-bisacrylates by the reaction of bisphenols with acrylic acid halides in the presence of bases.

Bisphenol-bisacrylates are known, e.g. the bisacrylates of bisphenol A. They are starting materials for the preparation of cross-linked polymers. They polymerise very readily so that undesirable side reactions take place during their preparation and purification. Since uncontrolled polymerisation may also occur in spite of the addition of inhibitors, their preparation is difficult, especially on a technical scale (e.g. GB-P No. 738 954).

It is also known from GB-P No. 738 954 that the side reactions can be suppressed at low temperatures (below 50° C.). In this way, for example, 53% of the theoretical yield may be obtained in the production of bisphenol A—bismethacrylate from methacryloyl chloride with the anhydrous disodium salt of bisphenol A in benzene.

It is known from JP-OS No. 73-48453 that bisphenol A—bismethacrylate may be prepared in high yields from methacrylic acid and bisphenol A in boiling benzene using gaseous HCl as catalyst but the application of this process, especially on a technical scale is problematic because bisphenol is readily split up and isomerised in the presence of strong acids at elevated temperatures.

It is also known to condense acid halides and phenolic compounds in a disperse phase of water and a water-immiscible organic solvent in the presence of inorganic bases such as sodium hydroxide (e.g. J. Amer. Chem. Soc. 81, 4310-3 (1959)). This process, however, cannot be used for reacting bisphenols quantitatively to bisacrylates since a certain amount of the semiester of the bisphenol is always formed in addition to the bisester owing to partial hydrolysis of acryloyl chloride by the basic aqueous solution. Since this semiester is not easily removed it interferes with the polymerisation of the bisacrylate by acting as a phenolic inhibiting substance. Isolation of the reaction product from the solution by evaporative concentration is always accompanied by partial polymerisation even under mild conditions.

It is known from U.S. Pat. No. 4,068,082 to prepare bisphenol acrylates in polar aprotic solvents such as acetone in the presence of amines. Separation of the amine and the amine salt from the reaction mixture is difficult and large quantities of solvent are obtained which must be worked up since the reaction mixture is poured on to an enormous quantity of ice water, compared with the quantity of reaction mixture.

It has now been found that bisphenol-bisacrylates may be prepared in high yields from acryloyl chlorides and bisphenols in the presence of tertiary amines in apolar solvents and the problems described above can at the same time be avoided.

The present invention relates to a process for the preparation of bisphenol-bisacrylates by the reaction of bisphenols with acrylic acid halides in the presence of bases, characterised in that the reaction is carried out in an apolar solvent in the presence of a tertiary amine and in the absence of an aqueous phase, the amine salt is subsequently removed by extraction with water, and the bisphenol-bisacrylates are obtained in a crystalline form from the organic phase.

The salts of bisphenols and tertiary amines are soluble at least slightly soluble in apolar solvents although the bisphenols as such are virtually insoluble in such solvents.

Suitable bisphenols are those with 2 or 3 aromatic nuclei, such as 4,4'-dihydroxy-diphenyl, 4,4'-digydroxy-diphenylether, 4,4'-dihydroxy-diphenylsulphide, dihydroxy-diphenylsulphone, dihydroxy-diphenylethane, dihydroxydiphenylmethane and halogen substituted bisphenols such as tetrachloro- and tetrabromo-bisphenal A, the following being preferred: 4,4'-Dihydroxy-3,3'-diphenyl-diphenylpropan, 4,4'-Dihydroxy-3,5,3',5'-Tetramethyl-diphenylpropan, 4,4'-Dihydroxy-3,3',5,5'-tetramethyl-diphenylmethan, 5,5'-Dihydroxy-1,1,1',1'-tetramethyl-spiro-bis-indan, 5-hydroxy-1,1,3-(4'-hydroxyphenyl)-indan, 4,4'-dihydroxy-diphenylethane, 4,4'-dihydroxy-diphenylcyclohexane-(1,1), $\alpha,\alpha$-bis(4-hydrosyphenyl)-m-and-p-diisopropylenzene, and especially bisphenol A.

Acryloyl halides such as acryloyl bromide, acryloyl chloride and methacryloyl bromide are preferred acrylic acid derivatives, and methacryloyl chloride is especially preferred.

The amines used according to the invention may be tertiary amines such as heterocyclic and aliphatic amines with up to 15 carbon atoms, e.g. pyridine, $\alpha$-, $\beta$- and $\gamma$-picoline N-methyl-morpholine, diethylcyclohexylamine, isopropyldiethylamine and dimethylbutylamine; preferably aliphatic amines with up to 12 carbon atoms such as diisopropylamine, tripropylamine, tributylamine and especially triethylamine.

Apolar solvents in the context of the present invention are water immiscible compounds having 4 to 10, preferably 5 to 8 carbon atoms at least two of which are aliphatic carbon atoms; for example, tetraline, isopropylbenzene, decaline, di-tert.-butylether, diisobutylene, triisopropylene and decane, preferably cycloheptane, cyclooctane, isopropylcyclohexane and ethylcyclohexane and most preferably pentanes, hexanes, petroleum ether, ligroin, isooctane, n-octan,e cyclohexane, methylcyclohexane and methylcyclopentane.

The mother liquor obtained after separation of the bisacrylates may advantageously be used as reaction medium. This enables the process to be carried out more economically and enables even higher yields of bisacrylate to be obtained. In order to avoid the progressive accumulation of by-products in the reaction medium, part of the mother liquor may be removed after each reaction cycle and worked up separately.

The process may generally be carried out by first introducing the bisphenol, amine and solvent into the reaction vessel and then adding the acryloyl halide with stirring, optionally diluted with the solvent. The ammonium halide then precipitates and generally also part of the bisphenol-bisacrylate. Since the reaction proceeds rapidly, the acryloyl halide may be added rapidly with efficient cooling.

The reaction according to the invention may be carried out continuously, for example in reactors equipped with circulating pumps or in tube reactors equipped with mixing elements, the bisphenol solution and the acryloyl halide being added simultaneously.

Water may subsequently be added to the reaction solution in sufficient quantity to dissolve the amine salts and the reaction mixture may at the same time be heated to 60° C., preferably to 50° C. to dissolve the bisacrylates partly or completely. Two clear, easily separated phases are obtained. The organic phase may be freed from any cloudiness by simple filtration if necessary. After cooling of the organic phase, the bisacrylate is separated by any of the usual processes such as filtration, decanting or centrifuging.

In view of the high degree of purity of the crude products, isolation of the bisacrylates may also be carried out by careful rapid evaporation of the solvent, e.g. by spray drying.

The mother liquor obtained may be used again for further reactions. The aqueous phase is made alkaline by the addition of an alkali and the amine can be clearly separated as a second phase and thus isolated. Any remaining residues of amine may be extracted with the solvent if necessary. The amine is thus recovered virtually quantitatively and may be used again after azeotropic dewatering.

The reaction temperature is in the region of from $-10°$ to $60°$ C., preferably from $-5°$ to $50°$ C., most preferably from $0°$ to $45°$ C.

The bisphenol, acrylic acid halide and amine used as reactants are put into the process in stoichiometric ratios ranging approximately from 1:2:2 to 1:2.2:2.4.

Conventional stabilizers such as copper salts, quinones, phenols or aromatic amines may be added to stabilize the bisacrylates during the reaction and while they are worked up. Examples of such stabilizers include copper-I chloride, toluquinone, hydroquinone monomethylether and phenothiazine. The process may be carried out with access of air.

The bisphenol-bisacrylates obtained according to the invention are pure and may be used for many purposes without further purification. They may be converted into highly pure products by recrystallisation from suitable solvents, e.g. the solvents used in the reaction or lower alcohols such as methanol, ethanol or isopropanol.

EXAMPLES

EXAMPLE 1

22.8 g (0.10 Mol) of bisphenol A are dissolved in 21.0 g (0.21 mol) of triethylamine with stirring and diluted with 100 to 120 ml of cyclohexane. 21.0 g (0.20 mol) of freshly distilled methacrylic acid chloride to which 0.1% by weight of hydroquinone monomethylether has been added are introduced dropwise with stirring in the course of 30 minutes while the reaction mixture is cooled with ice to maintain the temperature at 15° to 20° C. After one house, 25 g of water are added and the mixture is heated to 40°–45° C. The aqueous phase is separated off and neutralised with a sufficient quantity (at least 0.21 mol) of an inorganic base such as sodium or potassium hydroxide and the amine phase which floats to the top is removed. 20.5 g of amine is recovered by this method.

According to gas chromatographic investigation, the organic phase contains pure bisphenol-A-bismethacrylate which contains only 0.2% by weight of bisphenol-A-monomethacrylate (semiester).

By cooling of the organic phase and suction filtration, 27.8 g (i.e. 76% of theoretical) of bisphenol-A-bisacrylate are obtained as colourless crystals (m.p.: 74°–75° C.).

EXAMPLE 2

Example 1 is repeated, using the cyclohexane mother liquor from Example 1 as solvent and replacing any losses due to evaporation.

After the reaction and separation of the amine salt, the organic phase contains bisphenol-A-bismethacrylate and 0.3% by weight of the semiester. 35.6 g (98% of theoretical) of colourless crystals (m.p.: 74°–75° C.) are obtained after cooling, suction filtration and drying.

EXAMPLE 3

Example 1 is repeated but using 80 ml of cyclohexane and 38.0 g (0.20 mol) of tributylamine instead of 0.21 mol of triethylamine. After the reaction has continued for 5 hours at 20° C. and the product has been worked up as in Example 1, the cyclohexane solution contains 1% by weight of the semiester. 27.6 g (76% of theoretical) of colourless crystals (m.p.: 74° C.) are isolated.

When this example is repeated with the mother liquor as in Example 2, the yield of bisacrylate is increased as in Example 2.

Comparison Example 1

22.8 g (0.10 Mol) of bisphenol A are dissolved in a solution of 8.8 g (0.22 mol) of NaOH and 20 ml of water. 1.0 g of triethylamine which serves as catalyst and 80 ml of cyclohexane are then added, followed after 2 hours by 22.0 g (0.21 mol) of methacrylic acid chloride which is added at 15° to 20° C. After the product has been worked up as in Example 1, the organic phase contains 0.5% by weight of bisphenol A and 5% by weight of monomethacrylate in addition to bisphenol A-bismethacrylate 27.8 g (i.e. 76% of theoretical) of bismethacrylate (m.p.: 48°–56° C.) are isolated from the cyclohexane solution as in Example 1.

Comparison Example 2

When Comparison Example 1 is repeated, the organic solution is found to contain 3% by weight of bisphenol A and 4% of monomethacrylate in addition to the bismethacrylate. The results are more difficult to reproduce than those of the process according to the invention because the diphasic reaction is influenced by factors which are difficult to oversee.

Comparison Example 3

When Comparison Example 1 is repeated with an excess of 20 mol-% of methacrylic acid chloride and NaOH to increase the conversion into bis-methacrylate, no improvement is obtained. The reaction solution contains 2% of bisphenol A and 4% of monoacrylate in addition to the bisacrylate.

Comparison Example 4

When methylene chloride is used as solvent in Comparison Example 1 instead of cyclohexane, the reaction product can only be isolated by evaporative concentration. Although this is carried out under vacuum at room temperature in the presence of stabilizers such as toluquinone and hydroquinone monomethylether, a partially polymerised evaporation residue is invariably obtained even when the experiment is repeated several times.

Comparison Example 5

When Comparison Example 1 is repeated but 32 g (0.30 mol) of powdered anhydrous sodium carbonate are used instead of NaOH and 2 g of triethylamine are used in the absence of water and the reaction is continued for 6 hours at 20° to 30° C., he organic phase contains 3% by weight of bisphenol A and 4% by weight of the semiester in addition to bisphenol A-bismethacrylate. The isolated product melts at 45° to 53° C.

Comparison Example 6

114 g (0.50 Mol) of bisphenol A and 172 g (2.0 mol) of methacrylic acid in 200 ml of benzene are saturated with HCl gas and the mixture is slowly heated to boiling with concomitant introduction of HCl and boiled for 4 hours. 70 g of impure bisphenol A (m.p.: 130°–140° C.) are isolated on cooling. No bisphenol A-bismethacrylate can be detected gas chromatographically in the mother liquor.

We claim:

1. Process for the preparation of bisphenol-bisacrylates by the reaction of bisphenols with acrylic acid halides in the presence of bases, characterised in that the reaction is carried out in an apolar solvent in the presence of a tertiary amine and in the absence of an aqueous phase and the amine salts are subsequently removed by extraction with water while the bisphenol-bisacrylates are obtained in a crystalline form from the organic phase.

2. Process according to claim 1 characterised in that the tertiary amines are aliphatic amines containing up to 12 carbon atoms.

3. Process according to claim 1, characterised in that triethylamine is used.

4. Process according to claim 1, characterised in that bisphenol A is used.

5. Process according to claim 1, characterised in that the solvents used are pentanes, hexanes, petroleum ether, ligroin, cyclohexane, methylcyclohexane, methylcyclopentane and octanes.

6. Process according to claim 1, characterised in that the mother liquor obtained after separation of the bisphenol-bisacrylates is used again as reaction medium.

* * * * *